United States Patent [19]
Blackman et al.

[11] Patent Number: 6,146,386
[45] Date of Patent: Nov. 14, 2000

[54] CABLE OPERATED BONE ANCHOR COMPRESSOR

[75] Inventors: Ronald G. Blackman, Oakland, Calif.; John Stewart Young, Memphis, Tenn.; David L. Brumfield, Southhaven, Miss.

[73] Assignee: SDGI Holdings, Inc., Wilmington, Del.

[21] Appl. No.: 09/244,632

[22] Filed: Feb. 4, 1999

[51] Int. Cl.$^7$ .................................................. A61B 17/58
[52] U.S. Cl. ................. 606/103; 606/61; 606/74
[58] Field of Search ................. 606/61, 74, 103; 140/93.2, 123.5, 123.6

[56] References Cited

U.S. PATENT DOCUMENTS

| | | | |
|---|---|---|---|
| 3,661,187 | 5/1972 | Caveney et al. | 140/123.6 |
| 4,050,464 | 9/1977 | Hall | 128/303 |
| 4,793,385 | 12/1988 | Dyer et al. | 140/123.6 |
| 5,484,441 | 1/1996 | Koros et al. | 606/79 |
| 5,584,839 | 12/1996 | Gieringer | 606/96 |
| 5,591,167 | 1/1997 | Laurain et al. | 606/61 |

OTHER PUBLICATIONS

Sofamor Danek 1997 Catalog, pp. 50, 102, 144, 168.

*Primary Examiner*—Michael Buiz
*Assistant Examiner*—Julian W. Woo
*Attorney, Agent, or Firm*—Woodard, Emhardt, Naughton, Moriarty & McNett

[57] ABSTRACT

A cable operated bone anchor compressor and a method for thoracoscopically compressing bone anchors are disclosed. In procedures in which bone anchors, such as bone screws, are fixed to bone tissue and such bone tissue is to be readjusted or realigned, the device of the present invention is thoracoscopically inserted. The device includes a cable to be placed in contact with one bone anchor, and an elongated member with a mating head to be placed against another bone anchor. When the cable is retracted, the bone anchors are compressed or pulled toward each other to realign, in a desired fashion, the bone tissue to which they are attached.

49 Claims, 6 Drawing Sheets

CABLE OPERATED BONE ANCHOR COMPRESSOR

FIELD OF THE INVENTION

The present invention relates to minimally-invasive surgery to correct bone ailments or abnormalities. Specifically, the present invention comprises a cable operated device and method of compressing bone anchors connected to bone tissue, used in correcting abnormalities such as an improper curvature of the spine.

BACKGROUND OF THE INVENTION

In the treatment of abnormal curvatures of the spine, such as kyphosis, lordosis, and scoliosis, it is common to perform a surgical procedure on the patient whereby the curvature of the spine is altered so as to render it as normal as possible. For example, in the correction of scoliosis, anterior spinal instrumentation and fusion of two or more vertebrae has been a standard approach for at least the last 35 years. In such procedures, a thoracotomy incision is made, and a portion of the spine is exposed, particularly around the apex of the curve. The surgeon then may excise some or all of one or more intervertebral discs in the exposed spinal region. After removing the disc tissue, if that procedure is performed, the improperly curved vertebrae can then be implanted with corrective instrumentation and repositioned.

The surgeon selects appropriate bone anchors, commonly screws for fixation within a pedicle or other spinal portion, and fixes the bone anchors within two or more vertebrae to be repositioned. A rod or pin, which may be pre-contoured and/or contourable in situ, is fitted with the fixed bone anchors and held thereto. This is commonly accomplished by fitting a cap, set screw, or similar piece to the bone anchor, so that the rod is contained with the bone anchor, yet retains some freedom to move in response to the repositioning of the vertebrae.

After this instrumentation is implanted, the surgeon repositions the vertebrae. Repositioning occurs by compression of the bone anchors—i.e., the bone anchors are pushed toward each other—thereby moving the vertebrae to which they are fixed. To compress the bone anchors, it is known to use, among other relatively large tools, a scissor- or tongs-like device. Generally, the compressing device has two lever arms connected in an X-shape that can pivot with respect to one another. One end of each lever arm is gripped by the surgeon, and these hand-gripping ends are spread apart. The compressing ends, which are the ends opposite the hand-gripping ends, are placed in contact with the bone anchors. The surgeon then moves the gripping ends together, thereby forcing the compression ends and their corresponding bone anchors toward each other. In this way, the relative positions of two vertebrae are altered. Compression continues until the vertebrae correspond to the curvature of the spinal rod and/or to a normal or approximately normal spinal curvature. When the compression is finished, the set screws or caps fitted to the bone anchors can be tightened, fixing the bone anchors to the rod, and fixing the spine in its new curvature. Fusion of vertebrae or other treatment of the intervertebral spaces from which disc tissue was excised can then be performed.

Performing these tasks using traditional techniques and devices of open surgery has severable undesirable features and consequences. Initially, such open surgery requires a long thoracotomy, which incision leaves a relatively long and unappealing scar. Further, such surgery entails incision, retraction, and adjustment of numerous tissues in addition to the spinal tissues. As a result, trauma to these tissues and resulting pain and possibility of infection are relatively high. Still further, a standard thoracotomy may expose only one apex of the spinal curve to be corrected, thus requiring additional incisions or a longer initial incision in order to be able to fully treat the spine. Even where the apex of the spinal curve is adequately exposed and in good position relative to the thoracotomy for surgery, commonly adjacent vertebrae and intervertebral discs are not parallel to the exposure view provided by the thoracotomy, decreasing the effectiveness of the instrumentation used to correct the abnormal curvature. For these reasons, an endoscopic, thoracoscopic or other minimally invasive approach is preferable.

Accordingly, what is needed is a device and method that allows compression of orthopedic bone anchors through a single standard endoscopic, thoracoscopic or laparoscopic port.

SUMMARY OF THE INVENTION

The present invention comprises an instrument and method for compressing bone anchors fixed with respect to bone tissue, such as spinal bone tissue, that can be operated through a minimal thoracotomy or port. Specifically, the instrument comprises an elongated member having an end portion configured to mate with one of the bone anchors, and a cable adapted to fit with the elongated member so that the cable extends along at least a portion of the elongated member and extends beyond its end portion, wherein the cable is retractable with respect to the elongated member. The cable preferably includes a loop extending beyond the elongated member, and has an adjustable length. The elongated member is preferably L-shaped, hollow and sized to fit through a standard laparoscopic or thoracoscopic port, and also includes two apertures, so that the cable extends through the elongated member and exits it through the apertures. The end portion of the elongated member may be generally perpendicular to the elongated member, and include surfaces having depressions in them. Both the cable and the elongated member are made of sturdy material, preferably metal, which material may be biocompatible.

The instrument of the present invention allows minimally-invasive introduction and performance of the task of compressing the bone anchors, eliminating the need for a large incision in order to accommodate a compressing tool. The adjustable cable allows for use in all situations where compression of bone anchors is indicated, regardless of the distance between the bone anchors. The forces required for compression are transmitted through the cable directly to the bone anchors, so that those forces are applied at the proper points and in the proper directions. The shape of the elongated member and its end portion also allow for varying placement of a thoracotomy or surgical port.

The method according to the present invention comprehends thoracoscopically correcting abnormal bone placement by compressing bone anchors fixed in bone tissue. The method comprises providing a device having an end portion configured to mate with bone anchors and a retractable cable beyond said end portion; inserting the cable and end portion into the patient; placing the cable in contact with one bone anchor; placing said end portion in contact with a second bone anchor; and retracting the cable, thereby pulling the bone anchor to which the cable is in contact toward the bone anchor contacted by the end portion. A loop can also be provided in the cable, and the method of the present invention can be performed on multiple sets of bone anchors as may be indicated by the injury or abnormality to be treated. Further, the method of the present invention can include placement and fixation of a rod so as to fix the treated tissue in its normal position.

An object of this invention is to allow performance of recognized therapeutic procedures for correcting abnormal bone positioning, such as scoliotic, kyphotic or lordotic spinal curvatures, in a less traumatic and less cosmetically-damaging way. A further object of the invention is to provide a device whereby bone anchor compression can be achieved minimally-invasively using a cable. Another object of the invention is to provide a device that can be inserted into the body through a small incision or port and that will compress bone anchors in the spine, and a method of endoscopically or laparoscopically compressing bone anchors in the spine, thereby correcting an abnormal spinal curvature. Further objects and advantages of the present invention will become apparent to those whose skill in the art after reading the following specification.

BRIEF DESCRIPTION OF THE DRAWINGS

FIG. 1A is a cut-away side view of an embodiment of the ratchet elements of the embodiment of the present invention illustrated in FIG. 1.

FIG. 5A is a front view of a portion of a spinal column, illustrating a use of the embodiment of the present invention illustrated in FIG. 1.

DESCRIPTION OF THE PREFERRED EMBODIMENT

Figure 1:
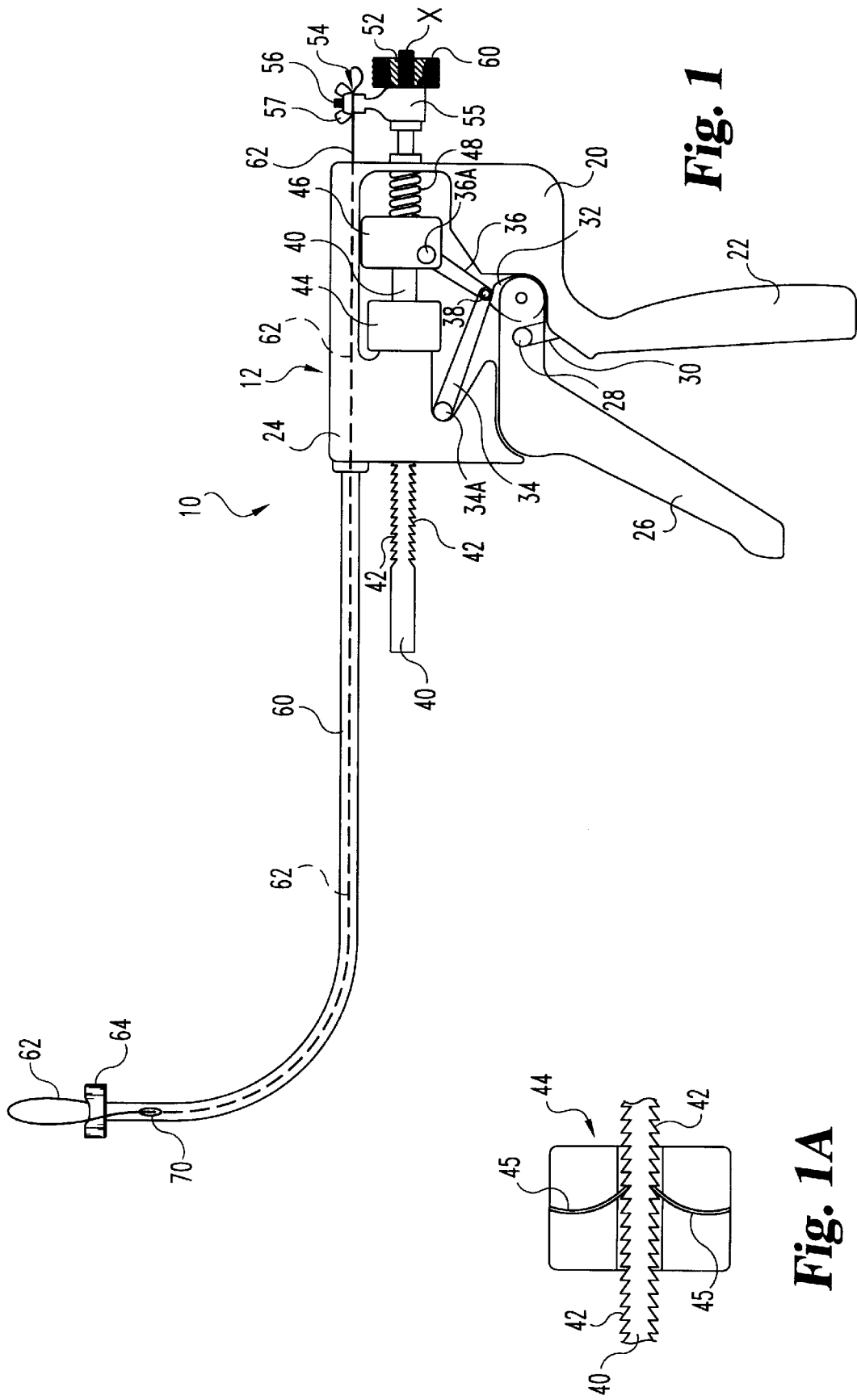
FIG. 1 is a side plan view of a preferred embodiment of the device of the present invention.

For the purposes of promoting an understanding of the principles of the invention, reference will now be made to the embodiment illustrated in the drawings and specific language will be used to describe the same. It will never- theless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Referring generally to FIG. 1, there is shown a cable operated compressor 10 according to one embodiment of the present invention. In the illustrated embodiment, compressor 10 includes a base element 12 and a tubular insertion element 14 which is attached to base element 12. Base element 12 is designed to retract and releaseably hold an adjustable cable. It will be apparent to one of ordinary skill in the art that alternative mechanisms, such as mechanisms incorporating rotational motion or electric power, may be used to accomplish this goal. The embodiment depicted in FIG. 1 is currently believed to be the best, and is the preferred mechanism for retracting and releaseably holding the cable.

Base element 12 comprises a frame 20, which includes a grip 22 and an upper portion 24. Connected to frame 20 in a pivoting relationship is an operator 26. Operator 26 pivots about axle 28, and axle 28 is attached to frame 20 via attachment arm 30. Operator 26 also includes a cam 32. When action part 26 is rotated about axle 28 so that as the lower portion of action part 26 rotates toward grip 22 of frame 20, cam 32 moves upward and away from grip 22 of frame 20. In contact with cam 32 are two lever arms 34 and 36. Lever arms 34 and 36 are connected to each other at a pivot point 38. Lever arm 34 is pivotably connected to upper portion 24 frame 20 at 34A, and lever arm 36 is pivotably connected to a ratchet element 46 at 36A, as further described below. As cam 32 moves upward when action part 26 is rotated about axle 28, cam 32 forces pivot point 38 in an upward direction, causing lever arms 34 and 36 to rotate with respect to each other about pivot point 38, increasing the angle between lever arms 34 and 36.

Also fitted within frame 20 is an elongated shaft 40. In the illustrated embodiment, shaft 40 is cylindrical and has sets of ratchet teeth 42 placed in opposing positions on the surface of shaft 40. Shaft 40 extends through frame 20, and is moveable in a generally axial direction within frame 20. Shaft 40, in the illustrated embodiment, is fitted within two ratchet elements 44 and 46. Ratchet element 44 is attached to frame 20, and includes a set of biased pawls 45, which may be in the form of leaf springs, that interact with ratchet teeth 42 (FIG. 1A). Ratchet element 46 is slidably received on shaft 40, substantially similar to or exactly like ratchet element 44, and therefore also includes a set of biased pawls that interact with ratchet teeth 42. Ratchet element 46 is pivotably connected to lever arm 36, as noted above, so that lever arm 36 is able to pivot with respect to ratchet element 46. A spring 48 is positioned around shaft 40 and is in compression between ratchet element 46 and a rearward portion of frame 20.

Shaft 40 extends beyond the rearward portion of frame 20, and in the embodiment shown in FIG. 1, terminates in a knob 50. Knob 50 may be a primarily cylindrical knob having one or more notches or slots 52 in its circumference. However, any known configuration, shape, surface, or other design of a knob may be used. Also fixed to shaft 40 is a cable anchoring element 54, which includes body 55, threaded post 56 and wing nut 57. Operation of cable anchoring element 54 is discussed hereinbelow.

Figure 2:
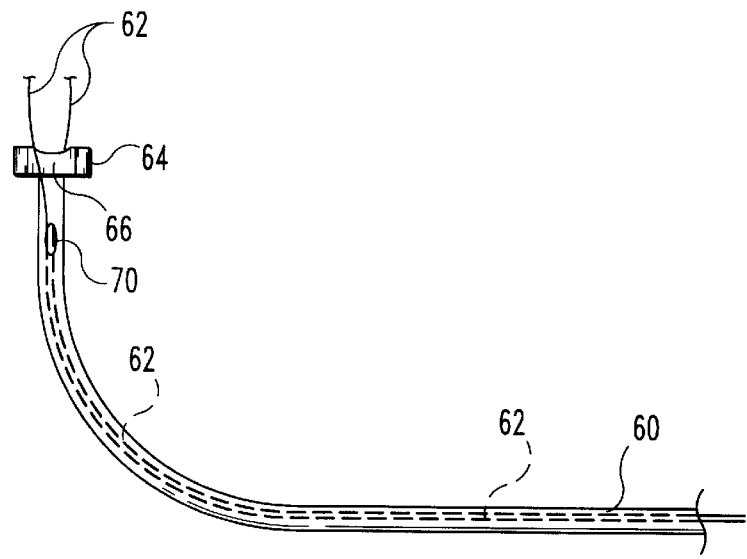
FIG. 2 is a side view of the end portion of the insertion element of the embodiment of the present invention illustrated in FIG. 1.
Figure 3:
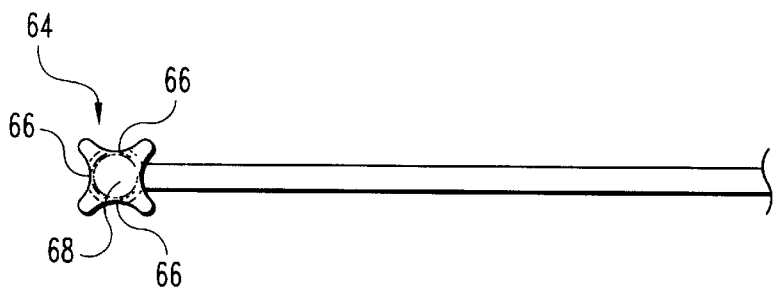
FIG. 3 is a top view of the end portion of the insertion element of the embodiment of the present invention illustrated in FIG. 1.

Insertion element 14 is attached to the front of frame 20 of base element 12. Insertion element 14 includes an elongated member 60 and a cable 62. Elongated member 60 is, in the illustrated embodiment, roughly L-shaped and hollow throughout of its length. At a forward or distal end of elongated member 60, there is positioned a mating part 64, which is more clearly depicted in FIGS. 2–4. Mating part 64, in the illustrated embodiment, is roughly in the shape of a square disc having rounded depressions 66 in each of the four sides, and a rounded depression 68 in the top or open side of mating part 64. Depressions 66 and 68 assist mating part 64 to achieve a relatively stable abutting relationship with bone anchors or with bone, as further described below. Elongated member 60 also includes two apertures 70 positioned proximate to mating part 64. In the illustrated embodiment, apertures 70 are oval-shaped and are positioned on opposite sides of the cylindrical elongated member 60 and in approximate alignment with two indentations 66 of mating part 64.

Figure 4:
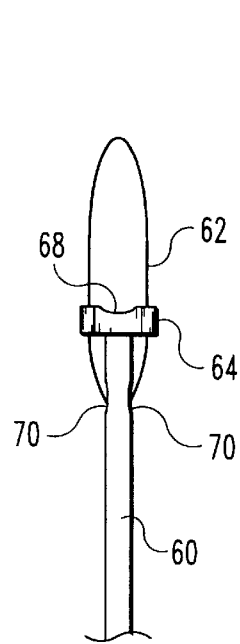
FIG. 4 is an end view of the end portion of the insertion element of the embodiment of the present invention illustrated in FIG. 1

As illustrated in FIGS. 1 and 4, cable 62 preferably forms a loop distal of mating part 64. In that embodiment, each end of cable 62 passes through an aperture 70, then through the hollow interior of elongated member 60 and frame 20, and are attached to cable anchoring element 54. A portion of cable 62 is wrapped around or otherwise paced in contact with post 56, and wing nut 57 is then threaded onto post 56 and tightened to clamp cable 62 to body 55. The length of cable 62 can be adjusted by loosening wing nut 57, taking in or letting out cable 62, and retightening wing nut 57. Cable 62 may also be connected directly to shaft 40, either inside or outside of frame 20, or it may be connected to a different part fixed on shaft 40. In an alternate embodiment, cable 62 could run along the side of elongated member 60 so long as cable 62 is guided along elongated member 60, as with eyelets.

Figure 5:
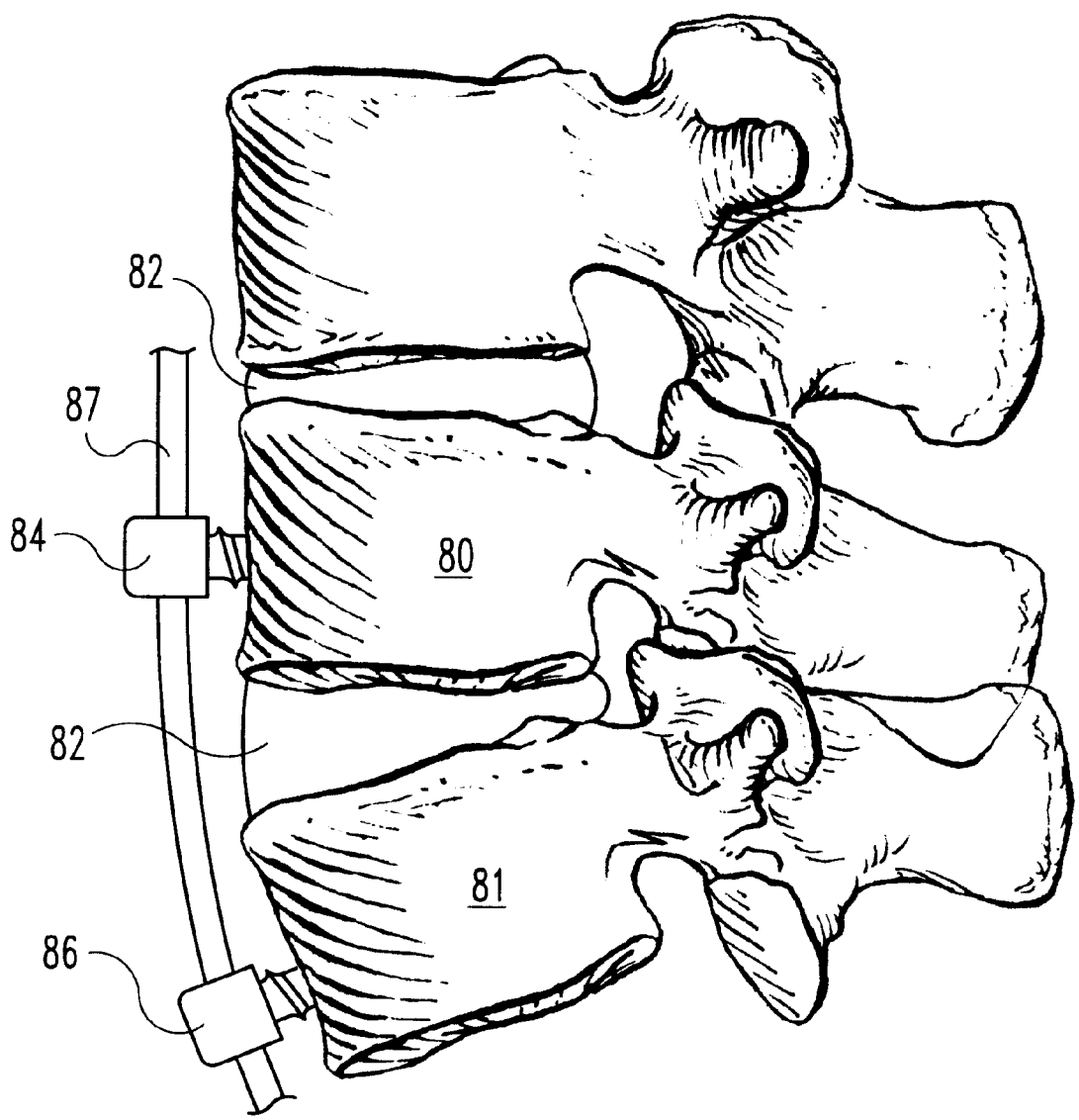
FIG. 5 is a side view of a portion of a spinal column exhibiting abnormal curvature, which has had bone anchors fixed thereto.

Referring generally to FIGS. 5–8, there is shown the general use of compressor 10 of the present invention. FIG. 5 depicts a section of the spine including vertebrae 80 and 81 separated by intervertebral discs 82. Endoscopic access, e.g. thoracoscopic or laparoscopic access, to the site is first obtained, through one or more small incisions, commonly in conjunction with standard endoscopic, laparoscopic or thoracoscopic ports. Thoracoscopic access is preferred, and the embodiments described herein generally refer to thoracoscopic access, although the incision and endoscopic access site can be at any position on the patient, depending on the site at which compression is desired. Portions of one or more of the intervertebral discs, particularly adjacent the excessively spaced sides of the vertebrae, may be excised, and bone anchors 84 and 86 are anchored to vertebrae 80 and 81 through one or more of the access incisions or ports. In the embodiment illustrated in FIG. 4, bone anchors 84 and 86 are bone screws, although other types of bone anchors such as hooks may be used with the present invention. When bone anchors 84 and 86 are fixed to the bone tissue at the desired locations, a rod or pin 87 is thoracoscopically inserted and fitted with bone anchors 84 and 86 so that rod 87 is held by bone anchors 84 and 86, yet enjoys some freedom of movement.

Compressor 10 is then introduced into the patient. Specifically, insertion element 14 of compressor 10 is inserted through one small thoracotomy or a port therethrough, and is maneuvered to a position proximate to bone anchors 84 and 86. Cable 62 is then placed around or in contact with bone anchor 86. In the embodiment of compressor 10 in which cable 62 forms a loop distal of mating part 64, the loop is placed around bone anchor 86 and may be retracted so that cable 62 contacts bone anchor 86. The mating part 64 of insertion element 14 is then placed in contact with the bone anchor 84, preferably by placing one of depressions 66 or 68 in mating contact with bone anchor 84. Then cable 62 is retracted, i.e., pulled toward mating part 64 of insertion element 14, thereby pulling with it bone anchor 86 toward bone anchor 84, as indicated by the arrow in FIG. 7. In this way, the entire compression force generated by compressor 10 and transmitted by cable 62 is applied directly to bone anchors 84 and 86, and is directed along the line connecting bone anchors 84 and 86. No compressive force is lost or improperly applied. The excessively spaced portions of vertebrae 80 and 81 are moved relative to each other, and into a normal or approximately normal alignment. When the desired compression has been administered, bone anchors 84 and 86 may then be placed in a state of complete fixation with rod 87, commonly by tightening the caps, set screws or other similar structure associated with bone anchors 84 and 86. Then the cable tension is released by turning knob 50 through up to 90 degrees, releasing the shaft 40 from the ratchet pawls. The cable can then be removed from the anchors and the thoracotomy or port. The process may be repeated as necessary on bone anchors 84 and 86. Further, the compressor 10 may then be moved to perform similar treatment on another set of bone anchors, which may include one of the bone anchors already compressed, or on another region of the spine.

Although it is preferred to perform compression using compressor 10 on bone anchors, compressor 10 may also be used to compress bone tissue, such as the processes or other parts of the spine, directly. For such use, mating part 64 of insertion element 14 should be adapted to abut such bone tissue. Compressor 10 is inserted into a patient and maneuvered toward the desired site for compression, as further described above. Referring generally to FIG. 5A, instead of placing cable 62 around or in contact with a bone anchor, cable 62 is placed around or in contact with bone 80a, as for example around transverse process 81a or other anatomical feature, and mating part 64 is placed in contact with another bone 80b, as for example around transverse process 81b or other anatomical feature. Then cable 62 is retracted, directly exerting force on processes 81a and 81b and their respective bones 80a and 80b, and moving them with respect to each other. Although bone 80a is illustrated in FIG. 5A as a vertebra, other bones may also be directly compressed.

Figure 6:
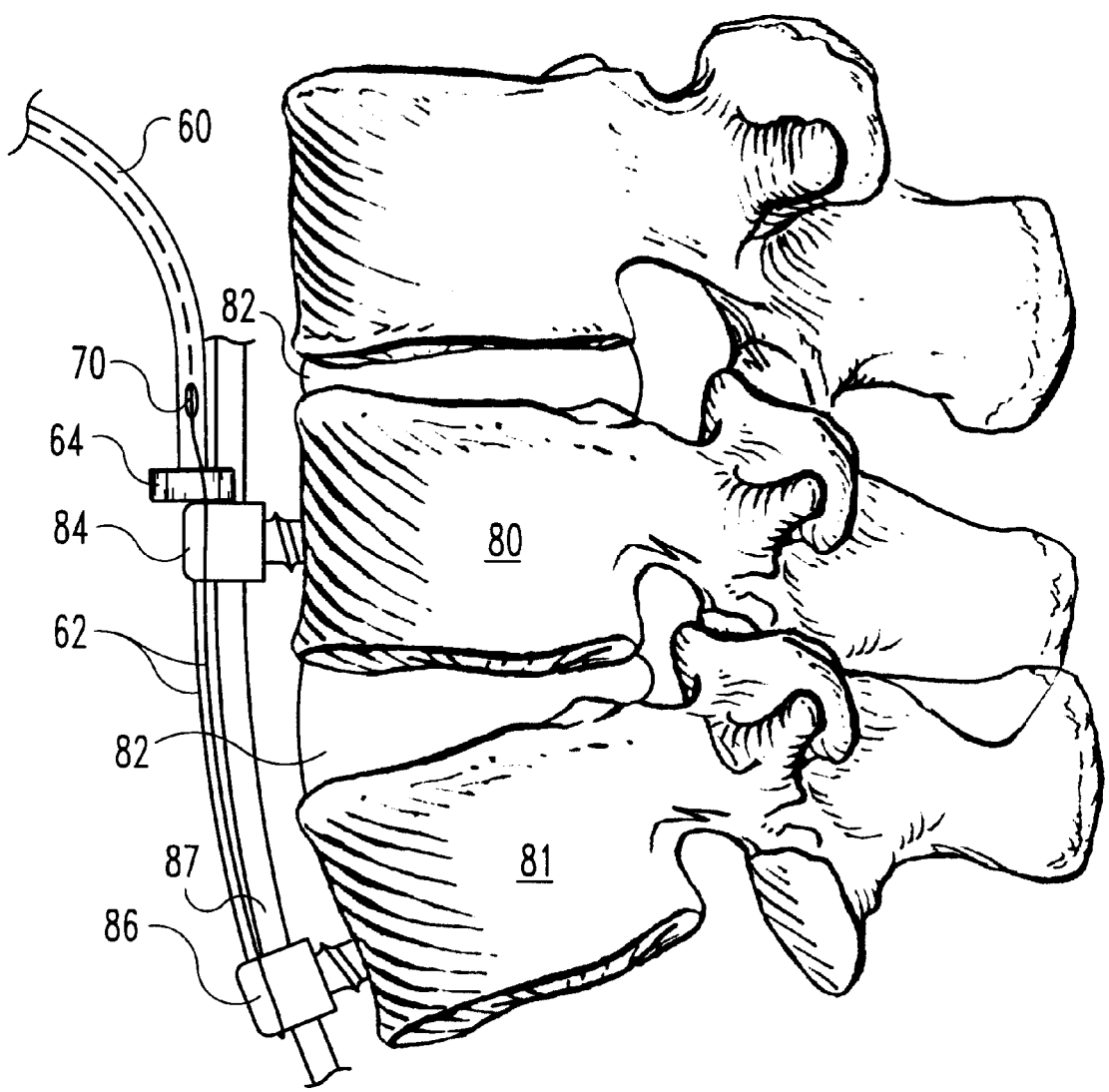
FIG. 6 is a side view of a portion of a spinal column as in FIG. 5, illustrating a use of the embodiment of the present invention illustrated in FIG. 1.
Figure 7:
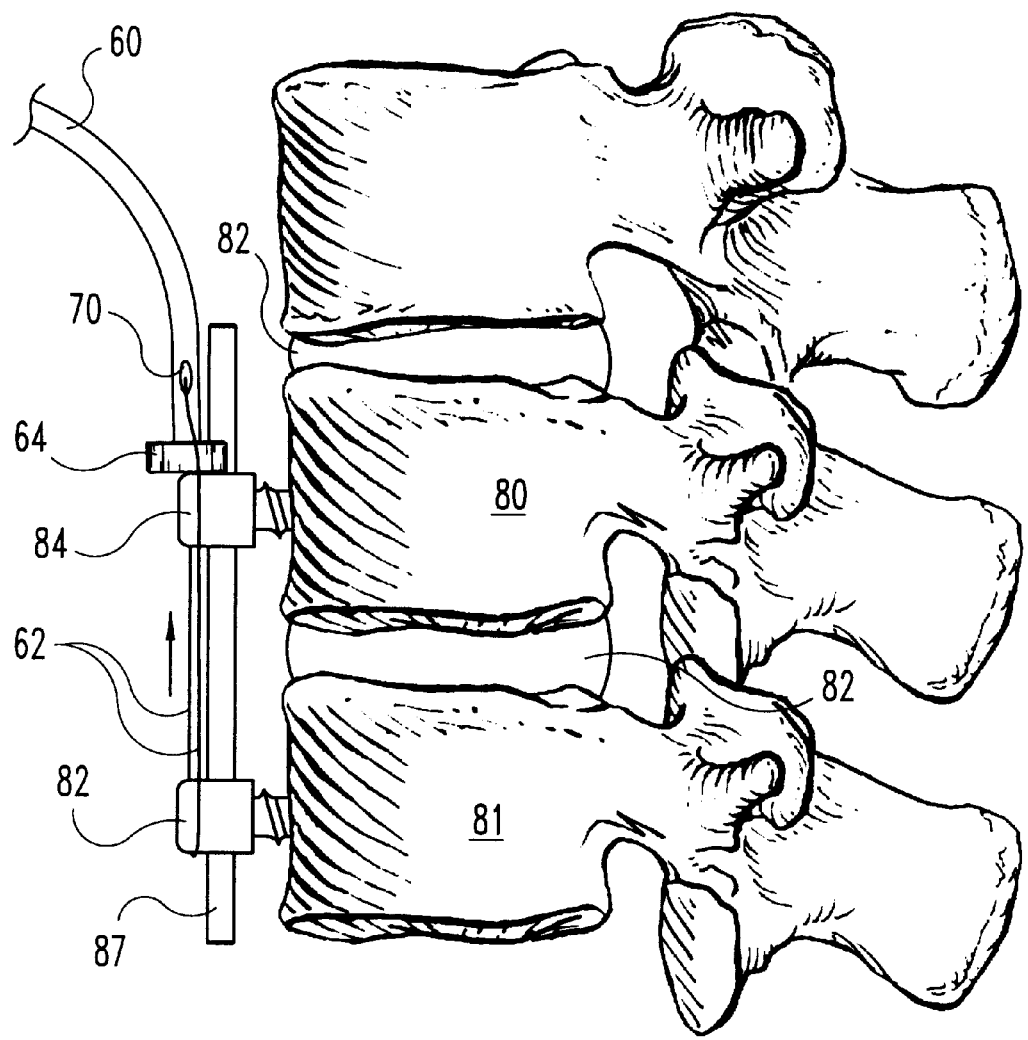
FIG. 7 is a side view of a portion of a spinal column corrected through use of the embodiment of the present invention illustrated in FIG. 1.
Figure 8:
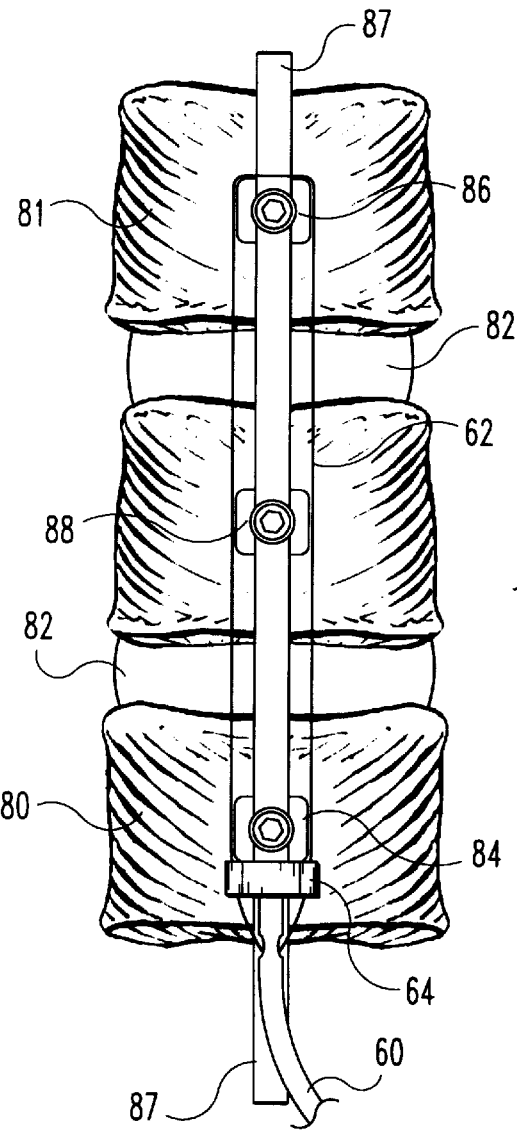
FIG. 8 is a top view of a portion of a spinal column as in FIG. 5, illustrating a use of the embodiment of the present invention illustrated in FIG. 1.

As illustrated in FIGS. 5–7, compression may be performed on a set of two adjacent bone anchors 84 and 86. Compressor 10 may also be used to compress non-adjacent bone anchors. As illustrated in FIG. 8, compressor 10 is placed in contact with bone anchors 84 and 86 in the manner described above, except an additional bone anchor 88 is positioned between bone anchors 84 and 86. Compressor 10 can therefore be used for compression of bone anchors positioned over several vertebrae as well as for compression of adjacent bone anchors.

Retraction of cable 62 is accomplished by the illustrated embodiment of compressor 10 in the following manner. Action part 26 is rotated with respect to frame 20 about axle 28. Such rotation forces cam 32 against lever arms 34 and 36 at pivot point 38. Lever arm 36 is therefore forced generally upward and away from lever arm 34 forcing ratchet element 46 generally toward the rear (i.e., to the right of FIG. 1) of frame 20. Pawls 45 of ratchet element 46 are forced against ratchet teeth 42 of shaft 40, and thus shaft 40 also moves in a rearward direction. Cable anchoring element 54, which is fixed to shaft 40, is therefore also forced backward, thereby pulling cable 62 in a rearward direction. Although the preferred embodiment of retraction mechanism is illustrated and described herein, it is understood that other mechanisms or parts may be utilized in order to accomplish the retraction of cable 62.

As shaft 40 is moved rearwardly, ratchet teeth 42 move pawls 45 of ratchet element 44, and therefore pawls 45 do not inhibit rearward movement of shaft 40. When action part 26 is released, spring 48 biases ratchet element 46 forward, which forward motion is permitted by pawls 45. Accordingly, pawls 45 of both ratchet elements 44 and 46 are biased toward ratchet teeth 42 and operate with the orientation of ratchet teeth 42 so that shaft 40 can move only rearwardly with respect to ratchet elements 44 and 46. When it is desired to release cable 62, knob 50 is turned about the axis of shaft 40 to a degree sufficient to disengage ratchet teeth 42 from pawls 45 of ratchet elements 44 and 46, and shaft 40 can then be manually moved forward. As shaft 40 moves forward, cable 62 also moves forward, slackening cable 62 and enabling disengagement of compressor 10 from bone anchors 84 and 86.

Figure 4A:
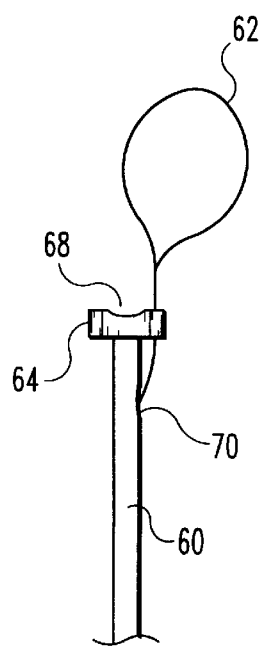
FIG. 4A is a view as in FIG. 4, illustrating an alternative configuration of the cable of the embodiment of the invention illustrated in FIG. 1.

As noted above, the illustrated embodiment of the invention includes a loop in cable 62 to facilitate compression of bone anchors 84 and 86. In the embodiment illustrated in FIG. 1, the loop is formed by doubling cable 62 on itself and clamping both ends of cable 62 in cable anchoring element 54. Alternatively, as illustrated in FIG. 4A, the loop is formed by joining one end of cable 62 to another part of cable 62, and clamping the other end of cable 62 in cable anchoring element 54. In either of those embodiments (i.e. FIG. 1 or FIG. 4A), the loop extends beyond mating part 64 of insertion element 14. In another embodiment of the invention, an unlooped cable 62 may be used. Unlooped cable 62 may be provided with a hook, enlarged area or other feature at its distal end for contacting and transmitting pulling force to bone anchor 84. The distal end of unlooped cable 62 may alternatively be wound around bone anchor 86 or otherwise gripped by bone anchor 86, as by holding with a cap or set screw.

Since it is to be used in a minimally-invasive surgical environment, elongated member 60 of compressor 10 is sized to be insertable through small incisions or ports and is preferably constructed of durable, sterilizable materials. Elongated member 60 in one embodiment is about 0.25 inches in diameter, and mating part 64 is in one embodiment about 0.375 inches between adjacent corners. In the most preferred embodiment, elongated member 60 is made of metal, and may be made of a biocompatible material such as stainless steel, although other relatively sturdy materials which will withstand the stresses of compressing bone anchors can be used. Cable 62 is preferably a metal cable which has a relatively small diameter but sufficient strength to overcome resistance to compression exhibited by bone or associated tissues. Other, non-metallic cables may also be used if strong enough. The term "cable" herein is intended to embrace any type of filamentary structure, in one or more individual strands or entwined, made of wire, fiber, reinforced polymer or other natural or synthetic materials.

Figure 9:
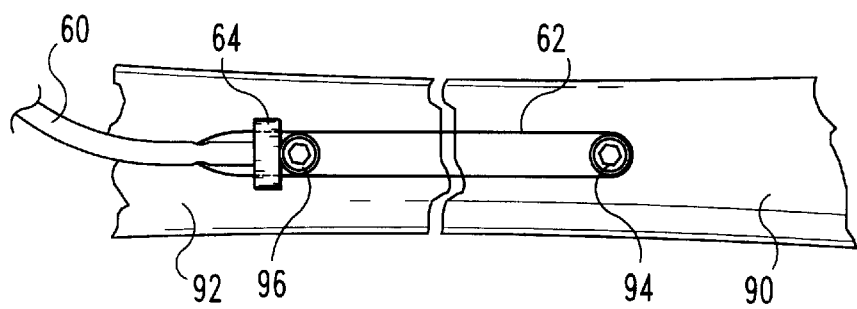
FIG. 9 is a top view of a portion of a fractured bone that has had bone anchors fixed thereto, and illustrating a use of the embodiment of the present invention illustrated in FIG. 1.

The device and method of the present invention are particularly useful in correcting abnormal curvatures of the spine. The device and method can also be useful in other environments such as in the repair of fractured or separated bone or other tissue. Referring generally to FIG. 9, there are shown separate parts 90 and 92 of a fractured bone, such as a long bone like a femur. Bone anchors 94 and 96 are fixed to bone parts 90 and 92, respectively. Compressor 10 is inserted through a small incision or port, maneuvered to the site of bone anchors 94 and 96, and cable 62 and mating part 64 are placed in contact with bone anchors 94 and 96, as described above. When cable 62 is retracted, bone anchors 94 and 96, and corresponding bone parts 90 and 92, move toward each other. In this way, parts of fractured bones can be pulled together to promote healing without open surgery.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for compressing bone anchors fixed to bone tissue, comprising:

an elongated member having a proximal portion and having a biocompatible distal portion, and having an end portion at said distal portion adapted to abut one of the bone anchors, said distal portion sized to be insertable through a minimally-invasive surgical incision; and a cable adapted to fit with said elongated member so that said cable extends along at least a portion of said elongated member and extends beyond said end portion of said elongated member; and a retractor attached to the proximal portion of said elongated member and said cable, whereby said cable may be retracted with respect to said elongated member.

2. The apparatus of claim 1, wherein said cable includes a loop in the portion of said cable extending beyond said end portion of said elongated member.

3. The apparatus of claim 2, wherein said cable is adjustable to change the size of said loop.

4. The apparatus of claim 3, wherein the retractor has:

a first member fixed to the proximal portion of said elongated member; and a second member connected to the cable, the second member being operable, when actuated, to move relative to the first member and thereby move the cable relative to said first member to change the size of said loop.

5. The apparatus of claim 4, wherein the retractor has a third member mounted on said first member and operable when said second member is not being actuated, to inhibit loop size change.

6. An apparatus for compressing bone anchors fixed to bone tissue, comprising:

an elongated member having a proximal portion and having a distal portion, and having an end portion at said distal portion adapted to abut one of the bone anchors; and a cable adapted to fit with said elongated member so that said cable extends along at least a portion of said elongated member and extends beyond said end portion of said elongated member; and a retractor attached to the proximal portion of said elongated member and said cable, whereby said cable may be retracted with respect to said elongated member, wherein said elongated member has a hollow portion with at least one aperture, and wherein said cable is coupled to said retractor and extends within said elongated member and out through said aperture.

7. The apparatus of claim 6, wherein said elongated member includes two apertures proximate to said end portion.

8. The apparatus of claim 1, wherein said end portion of said elongated member is generally perpendicular to said distal portion of said elongated member.

9. The apparatus of claim 8, wherein said end portion includes at least one surface having a depression.

10. The apparatus of claim 1, wherein said distal portion of said elongated member is generally perpendicular to said proximal portion of said elongated member.

11. The apparatus of claim 1, wherein said elongated member is generally L-shaped.

12. The apparatus of claim 1, wherein said elongated member is of a size wherein said elongated member is insertable through a standard laparoscopic or thoracoscopic port.

13. The apparatus of claim 12, wherein said proximal and distal portions of said elongated member have a diameter of approximately 0.25 inch.

14. The apparatus of claim 13, wherein said end portion of said elongated member has an approximately square configuration, the sides of which have a length of up to about 0.375 inch.

15. The apparatus of claim 1, wherein said cable has an adjustable length.

16. A method for endoscopically compressing bone anchors fixed to bone tissue, comprising:
   providing a device having an end portion adapted to abut one of the bone anchors and a retractable cable that extends distal of said end portion;
   inserting said cable and said end portion of said device endoscopically into a patient;
   placing said cable in contact with one of the bone anchors;
   placing said end portion in contact with a second of the bone anchors; and
   retracting said cable.

17. The method of claim 16, wherein said retracting step is repeated until a desired relative position of the bone tissue to which the bone anchors are fixed is achieved.

18. The method of claim 16, further comprising the step of providing a loop in said cable.

19. The method of claim 18, wherein said step of placing said cable in contact with one of the bone anchors comprises making said loop around a part of the bone anchor.

20. The method of claim 16, wherein said placing steps and said retracting step are performed on more than one set of bone anchors.

21. The method of claim 16, wherein said cable and said end portion of said device are inserted thoracoscopically into a patient.

22. A method of thoracoscopically correcting an abnormal spinal curvature, comprising:
   thoracoscopically accessing a region of the spine which is abnormally curved;
   fixing bone anchors to at least two vertebrae in said region of the spine;
   placing a rod in contact with said bone anchors such that said bone anchors contain said rod yet allow said rod limited movement relative to said bone anchors;
   providing a device having an end portion adapted to abut one of the bone anchors, and having a retractable cable that extends distal of said end portion;
   thoracoscopically inserting and maneuvering said cable and said end portion of said device into a position proximate to said region of the spine;
   placing said cable in contact with one of the bone anchors;
   placing said end portion in contact with a second of the bone anchors;
   retracting said cable until said region of said spine at least approximates a normal spinal curvature; and
   fixing said rod to said bone anchors to prevent relative movement therebetween, whereby said region of the spine is held in at least approximately a normal spinal curvature.

23. The method of claim 22, further comprising the step of providing a loop in said cable.

24. The method of claim 23, wherein said step of placing said cable in contact with one of the bone anchors comprises making said loop around a part of the bone anchor.

25. The method of claim 22, wherein said placing steps, said retracting step and said fixing step are performed on more than one set of bone anchors.

26. The method of claim 22, wherein said cable and said end portion of said device are inserted thoracoscopically into a patient.

27. An apparatus for compressing bone tissue, comprising:
   an elongated member having a proximal portion and having a distal portion, and having an end portion at said distal portion adapted to abut a portion of the bone tissue; and
   a cable adapted to fit with said elongated member so that said cable extends along at least a portion of said elongated member and extends beyond said end portion of said elongated member; and
   a retractor attached to the proximal portion of said elongated member and said cable, whereby said cable may be retracted with respect to said elongated member,
   wherein said elongated member has a hollow portion with at least one aperture, and wherein said cable is coupled to said retractor and extends within said elongated member and out through said aperture.

28. The apparatus of claim 6, wherein said cable includes a loop in the portion of said cable extending beyond said end portion of said elongated member.

29. The apparatus of claim 28, wherein said cable is adjustable to change the size of said loop.

30. The apparatus of claim 29, wherein the retractor has:
   a first member fixed to the proximal portion of said elongated member; and
   a second member connected to the cable, the second member being operable, when actuated, to move relative to the first member and thereby move the cable relative to said first member to change the size of said loop.

31. The apparatus of claim 30, wherein the retractor has a third member mounted on said first member and operable when said second member is not being actuated, to inhibit loop size change.

32. The apparatus of claim 6, wherein said end portion of said elongated member is generally perpendicular to said distal portion of said elongated member.

33. The apparatus of claim 6, wherein said cable has an adjustable length.

34. The apparatus of claim 27, wherein said cable includes a loop in the portion of said cable extending beyond said end portion of said elongated member.

35. The apparatus of claim 27, wherein said end portion of said elongated member is generally perpendicular to said distal portion of said elongated member.

36. The apparatus of claim 27, wherein said elongated member is generally L-shaped.

37. The apparatus of claim 27, wherein said distal portion of said elongated member includes at least a portion of said hollow portion and said aperture.

38. The apparatus of claim 1, wherein said cable includes means for contacting and transmitting pulling force to a bone anchor.

39. The apparatus of claim 2, wherein said cable has two ends, and said loop is formed by doubling said cable on itself and coupling both ends of said cable to a portion of said retractor.

40. The apparatus of claim 2, wherein said cable has two ends, and said loop is formed by joining one end of said cable to a portion of said cable, and coupling the other end of said cable to a portion of said retractor.

41. The apparatus of claim 8, wherein said end portion has an approximately square configuration including a plurality of sides and an end surface.

42. The apparatus of claim 41, wherein a plurality of said sides include a depression and said end surface includes a depression.

43. The apparatus of claim 6, wherein said distal portion of said elongated member includes at least a portion of said hollow portion and said aperture.

44. A method for compressing bone anchors fixed to bone tissue, comprising:

providing a device having an end portion adapted to abut one of the bone anchors and a retractable cable having a loop, said cable extending distally of said end portion;

inserting said cable and said end portion of said device into a patient;

placing said cable in contact with one of the bone anchors;

placing said end portion in contact with a second of the bone anchors; and retracting said cable.

45. The method of claim 44, wherein the step of providing a device includes providing the device of claim 1.

46. The method of claim 44, wherein said retracting step is repeated until a desired relative position of the bone tissue to which the bone anchors are fixed is achieved.

47. The method of claim 44, wherein said step of placing said cable in contact with one of the bone anchors comprises placing said loop around a part of the bone anchor.

48. The method of claim 44, wherein said placing steps and said retracting step are performed on more than one set of bone anchors.

49. The method of claim 44, wherein said cable and said end portion of said device are inserted thoracoscopically into a patient.

\* \* \* \* \*